United States Patent [19]

Walling

[11] Patent Number: 4,795,431

[45] Date of Patent: Jan. 3, 1989

[54] SYRINGE AND CATHETER APPARATUS

[76] Inventor: Peter T. Walling, 14126 Brookridge Circle, Dallas, Tex. 75240

[21] Appl. No.: 3,075

[22] Filed: Jan. 14, 1987

[51] Int. Cl.[4] ............................................. A61M 25/00
[52] U.S. Cl. ....................................... 604/97; 604/99; 604/208
[58] Field of Search .................................. 604/97-99, 604/208, 210, 121; 128/344

[56] References Cited

U.S. PATENT DOCUMENTS

| | | |
|---|---|---|
| 3,642,005 | 2/1972 | McGinnis . |
| 3,871,374 | 3/1975 | Bolduc et al. . |
| 3,905,361 | 9/1975 | Hewson et al. ................... 128/145.5 |
| 4,064,882 | 12/1977 | Johnson et al. . |
| 4,116,201 | 9/1978 | Shak ................................... 604/99 X |
| 4,205,683 | 6/1980 | O'Neil ................................... 604/99 |
| 4,335,723 | 6/1982 | Patel . |
| 4,370,982 | 1/1983 | Reilly ..................................... 604/98 |
| 4,439,185 | 3/1984 | Lundquist .............................. 604/97 |
| 4,583,974 | 4/1986 | Kokernak .............................. 604/211 |

OTHER PUBLICATIONS

Inflating Characteristics of Swan-Ganz Catheter Balloons: Clinical Considerations—Jean Francois Hardy, MD & Taillefer, M.D.
A study of the lateral wall pressure exerted by balloon-tipped catheters. Burdick, M.D., and Williams, M.D.
Pathophysiology of Rupture of the Pulmonary Artery by Pulmonary Artery Balloon-Tipped Catheters. Hardy, MD, Morissette MD, Taillefer MD and Vauclair, MD.
Pressure-Volume Relationships of the Pulmonary Artery Catheter Balloon-McDonald & Zaidan-Oct., 1982—18 Pages.
Pressure-Volume Relationships of the Pulmonary AR-tery Catheter Balloon-McDonald & Zaidan-Feb. 25, 1983—4 Pages.
American Edwards Soft-Wedge Syringe—descriptive and evaluation materials —1982—4 Pages.

Primary Examiner—Stephen C. Pellegrino
Attorney, Agent, or Firm—Hubbard, Thurman, Turner & Tucker

[57] ABSTRACT

To inflate the balloon element on the distal end of a pulmonary artery catheter an improved gas syringe is provided which is both volume and pressure-limited so that the syringe is capable of discharging into the catheter no more than the maximum design gas inlet volume thereof while at the same reducing the maximum attainable pressure within the catheter to a predeterminable level substantially below that reached when a conventional volume-limited syring of the same gas discharge capacity is used. The syringe volume delivery limitation is achieved by forming rearwardly disposed plunger stop members, or a suitable vent opening, in a sidewall portion of the syringe body. The pressure limitation is obtained by forming a pressure absorption zone which defines a substantially inextensible enlargement of the gas-receiving interior of the catheter. In one embodiment of the invention the pressure absorption zone is created in a forward end portion of the syringe body by a hollow stop member positioned therein, or inwardly projecting stop portions formed thereon, which engage and stop the syringe plunger rearwardly of the forward endwall of the syringe body. In an alternate embodiment, the forward plunger stop portion is deleted and the pressure absorption zone is formed externally to the syringe body by a length of tubing interconnected between the syringe outlet and the gas-receiving inlet of the catheter.

18 Claims, 1 Drawing Sheet

U.S. Patent     Jan. 3, 1989     4,795,431
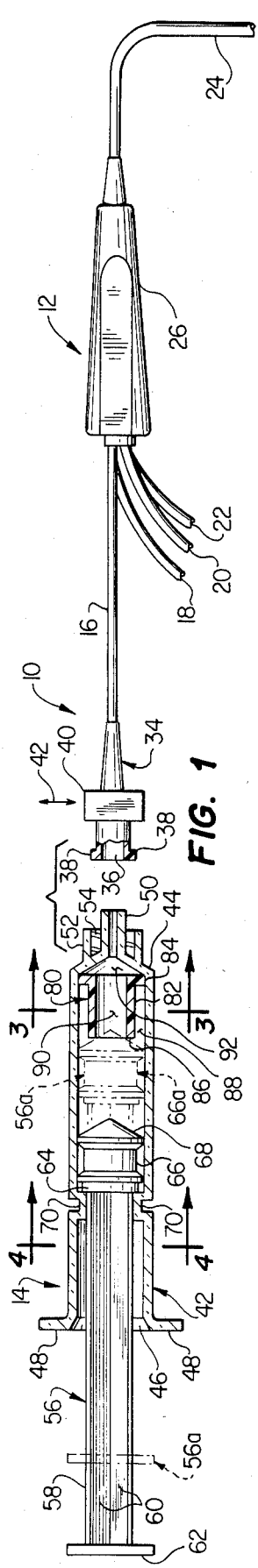
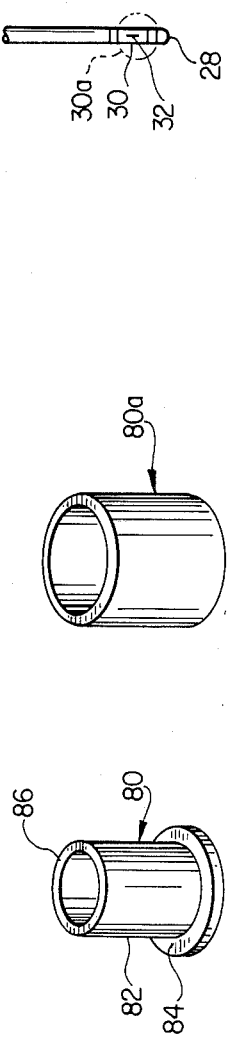
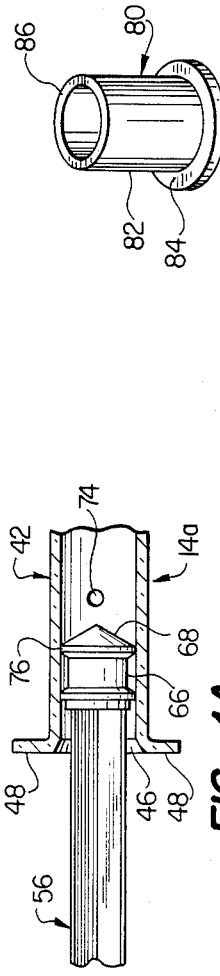
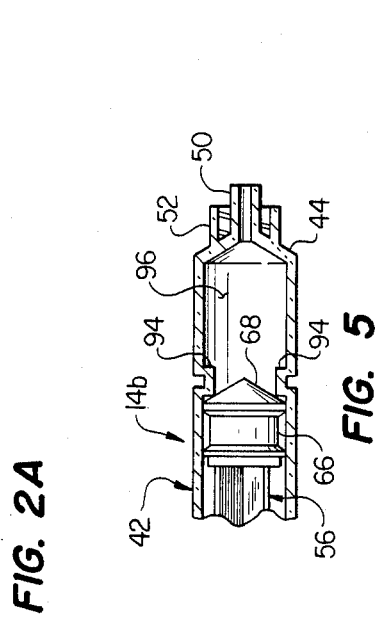
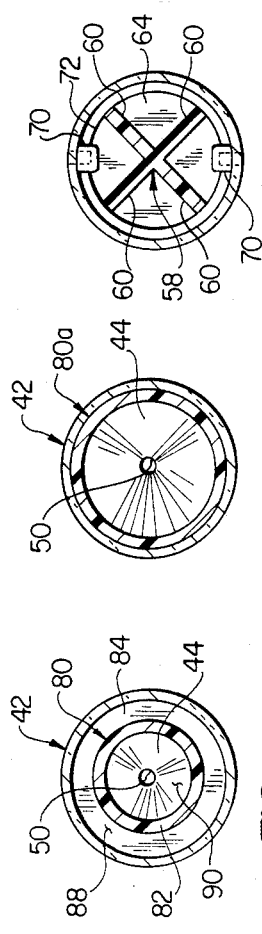
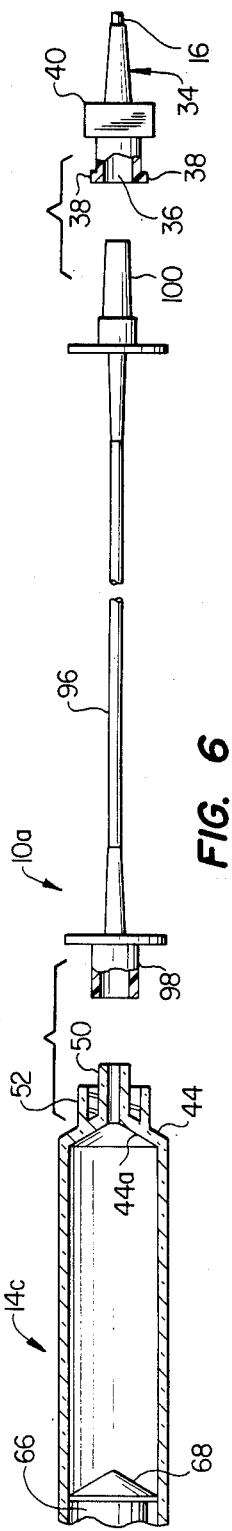

SYRINGE AND CATHETER APPARATUS

BACKGROUND OF THE INVENTION

The present invention relates generally to medical devices, and more particularly provides an improved syringe and inflatable catheter apparatus which incorporates a uniquely configured volume and pressure-limited gas syringe used to internally pressurize the catheter portion of the apparatus.

Potential over-pressurization of inflatable catheter elements used to internally block various body passages, such as the pulmonary artery, is a well known and long-standing problem in the practice of medicine. Pulmonary artery catheters are typically provided at their distal end with a small balloon which is selectively inflatable by a gas syringe connected to the catheter's gas-receiving inlet. To utilize the catheter, a sheath element is inserted into a suitable vein, such as the jugular vein, and the distal end of the catheter is fed through the sheath into the vein. When the distal end of the catheter exits the inner end of the sheath, the balloon is inflated. The inflated balloon acts as a "float" to assist in further insertion of the catheter by drawing its distal end through the vein (by virtue of the blood flow therethrough) and ultimately into a position in which the inflated balloon becomes "wedged" in a branch of the pulmonary artery. Lodged in a pulmonary artery branch in this manner the distal end of the catheter may be utilized in a conventional manner to monitor the pulmonary artery "wedge" pressure via the resulting pressure trace pattern on an oscilloscope operatively connected to the catheter.

After this initial wedge pressure reading is taken the balloon is deflated, but the catheter is normally left in place so that the balloon may be re-inflated to take subsequent wedge pressure readings. The over-pressurization problem previously mentioned typically arises when, between these intermittent balloon inflations, the distal catheter end "migrates" into a smaller portion or branch of the pulmonary artery. Subsequent balloon inflation then takes place in an unintended arterial portion which may be weaker and/or of a smaller interior cross-section than anticipated. If great care is not exercised in re-inflating the catheter balloon in these instances, the balloon can be over-pressurized and cause the artery to burst.

Typically, the catheter has a design inlet gas volume capacity corresponding to the gas volume required to fully inflate the balloon. In a variety of conventional manners the syringe is volume-limited to assure that no more than this designed-for gas volume can be forced into the catheter from the syringe to thereby prevent over-inflation of the balloon.

However, even with this volume "matching" between the syringe and catheter it is possible to cause over-pressurization of the catheter balloon during the intermittent reinflation thereof, and concomitant rupture of the artery portion into which it has migrated, if the syringe is not correctly and carefully used by its operator. Specifically, during each subsequent reinflation of the balloon the syringe plunger must be moved slowly toward the end of its stroke within the syringe body to avoid inordinately high "peak" pressures in the inflating balloon. Even the proper slow movement of the syringe plunger can cause the balloon to rupture the smaller or weaker artery portion if the plunger is pushed too far and too hard by the syringe operator.

The operational safety of conventional pulmonary artery catheters (as well as other types of syringe-operated inflatable catheters) is thus to a large degree dependent upon the "feel" transmitted to the syringe plunger as the catheter interior pressure is being increased, and the syringe operator's skill in interpreting and reacting to such "feel". Even though the pressure trace on the catheter-connected oscilloscope will normally indicate when the artery portion has been sufficiently occluded by the inflating balloon (by generating a recognizable "wedge" pattern), certain heart infirmities (such as an incompetent mitral valve) can generate a potentially misleading trace pattern which, even though the partially inflated balloon is fully blocking the artery portion, indicates that further balloon inflation is needed. It is this further balloon inflation which, in conventional volume-limited syringe and catheter apparatus, can easily burst the artery.

Various attempts have been previously made to eliminate this over-pressurization problem. For example, as exemplified in U.S. Pat. Nos. 3,642,005; 3,905,361 and 4,064,882 inflatable external indicator balloons have been placed on non-inserted portions of catheters to provide the syringe operator with an additional visual indication of the degree of inflation reached in the internal catheter balloon. Other supplemental visual internal catheter pressure indicia, such as simple pressure gauges have also been utilized. These and other visually oriented safety devices, however, must (along with the oscilloscope trace pattern) be continually watched by the syringe operator, and properly reacted to, to be effective. Also, particularly in the case of pressure gauges, moving parts are involved which are always subject to malfunction and wear.

Other mechanical devices, such as pressure relief valves, have also been used to actually limit the pressure supplied to the catheter. Illustrative devices of this type may be found in U.S. Pat. Nos. 3,871,374; 4,116,201 and 4,439,185. Other representative syringe and catheter devices may be found in U.S. Pat. Nos. 4,335,723; 4,370,982 and 4,583,974. The problem with mechanical pressure-limiting devices such as multi-component pressure regulators or relief valves is that they are subject, like all devices with moving parts, to malfunction or failure.

It can be seen from the foregoing that a long-standing need exists for improved syringe and inflatable catheter apparatus having greater operational safety from a catheter over-pressurization standpoint. Accordingly, it is an object of the present invention to provide such apparatus.

SUMMARY OF THE INVENTION

In carrying out principles of the present invention, in accordance with a preferred embodiment thereof, improved syringe and catheter apparatus is provided which comprises a catheter having an inflatable element such as a balloon on its distal end and an improved gas syringe which is connectable to the catheter and operable to inflate the distal end balloon thereon. The syringe is uniquely provided with both volume and pressure limiting means which cooperatively function to permit the syringe to force up to the maximum design volume of pressurized gas into the catheter while automatically reducing the maximum attainable gas pressure within the catheter (and thus the balloon) to a predetermined level well below that attainable when utilizing a conventional syringe with the same maximum gas volume discharge capability.

The volume limiting means in the improved syringe of the present invention are of generally conventional construction and may comprise either rearwardly disposed plunger stops formed within the syringe body to limit the rearward travel of the syringe plunger, a rearwardly disposed vent opening formed through a sidewall portion of the syringe body, or other suitable volume limiting means. In any event, the volume limiting means function to assure that no more than the maximum design gas volume of the catheter can be forced thereinto from the syringe.

The pressure limiting or pressure reducing means in the improved syringe function to create therein a pressure absorption zone which defines a substantially inextensible enlargement of the gas-receiving interior of the catheter. This volume enlargement creates, in effect, a "dead space" which reduces to a predetermined level the pressure rise within the catheter associated with its receipt of its design gas volume from the syringe. In the preferred embodiment of the present invention the pressure limiting means comprise forward stop means, disposed within the syringe body, for engaging and stopping the syringe plunger during forward travel thereof at a position spaced rearwardly from the forward endwall of the syringe body. By limiting the forward movement of the syringe plunger in this fashion the pressure absorption zone is formed within a forward end portion of the improved syringe. In one version of this improvement the forward stop means are defined by a hollow cylindrical stop member coaxially disposed within a forward end portion of the syringe body. In another version the forward stop means are formed by diametrically opposed, radially inwardly projecting sidewall portions of the syringe body which are spaced rearwardly from the forward endwall of the body.

In an alternate embodiment of the present invention the forward stop means are deleted from the syringe and the unique pressure absorption zone is formed externally to the syringe by a length of tubing operatively interconnected between the syringe outlet and the gas-receiving inlet of the catheter and having an interior volume equal to the desired volume of the pressure absorption zone.

The present invention conveniently permits the conversion of a standard syringe, having an internal volume greater than the design volume of a particular catheter, to a volume and pressure-limited syringe whose maximum dischargeable gas volume is precisely matched to the maximum design inlet volume of the catheter while at the same time reducing to a much safer, and predeterminable, level the maximum pressure attainable within the catheter. This conversion is easily and inexpensively achieved by simply forming the previously described volume limiting means on the syringe body and appropriately creating the pressure absorption zone either within the syringe body via the forward stop means, or externally to the body by using an appropriately sized length of interconnecting tubing.

Importantly, the unique operational safety improvement provided by the present invention is achieved without the addition of any complex, moving or wear-prone mechanical parts to the syringe and catheter apparatus such as mechanical pressure regulators, pressure relief valves, pressure gauges or external balloon inflation indicators. Moreover, other than the usual catheter-connected oscilloscope, there is no need for supplementary visual pressure-monitoring apparatus (such as pressure gauges or external balloon elements) which must be carefully and continuously watched by the syringe operator. All of these previously utilized mechanical pressure-monitoring devices are uniquely eliminated in the present invention due to its provision of the cooperating volume limiting means and the pressure absorption zone.

BRIEF DESCRIPTION OF THE DRAWINGS

FIG. 1 is a partially sectioned and exploded fragmentary side elevational view of an improved syringe and catheter apparatus which embodies principles of the present invention;

FIG. 1A is a partially sectioned side elevational view of a rear end section of an alternate embodiment of the syringe portion of the apparatus;

FIG. 2 is a perspective view of a hollow cylindrical pressure-limiting member disposed within the syringe of FIG. 1;

FIG. 2A is a perspective view of an alternate embodiment of the pressure-limiting member;

FIG. 3 is an enlarged scale cross-sectional view through the syringe, taken along line 3—3 of FIG. 1, and illustrates the pressure-limiting member of FIG. 2 disposed therein;

FIG. 3A is an enlarged scale cross-sectional view similar to that of FIG. 3, but with the pressure-limiting member of FIG. 2A disposed in the syringe;

FIG. 4 is an enlarged scale cross-sectional view through the syringe taken along line 4—4 of FIG. 1;

FIG. 5 is a partially sectioned side elevational view of a forward end portion of a further alternate embodiment of the syringe; and FIG. 6 is a partially sectioned and exploded fragmentary side elevational view of an alternate embodiment of the syringe and catheter apparatus.

DETAILED DESCRIPTION

Depicted in FIG. 1 is an improved syringe and catheter apparatus 10 which embodies principles of the present invention and comprises a pulmonary artery catheter 12, of conventional construction, and a uniquely configured syringe 14 which is utilized in a manner subsequently described to force air (or another, more readily soluble gas such as carbon dioxide) into the catheter 12. The representative catheter 12 illustrated in FIG. 1 is of the "quadruple lumen" type having, at its proximal or inlet end, four tubes or "lumens" 16, 18, 20, and 22 which are operatively interconnected to a single insertion tube 24 by means of a suitable connector fitting 26. Secured to the insertion tube 24, adjacent its distal end 28, is a small latex balloon member 30 which is inflatable to the dashed line configuration $30_a$ in response to the receipt of pressurized gas within the lumen 16 from the syringe 14. Pressurized syringe gas received within the lumen 16 is flowed into the balloon 30 via an internal passage (not illustrated) within the insertion tube 24 and a small slit 32 formed in the tube 24 and enveloped by the balloon.

At its outer end, the gas inlet or balloon inflation lumen 16 is provided with an inlet fitting 34 having a gas inlet passage 36 flanked by a pair of small connecting tabs 38, and a gas shutoff valve member 40 which is slidable relative to the balance of the inlet fitting 34, as indicated by the double-ended arrow 42, to selectively open and close the gas inlet passage 36. The other three lumens 18, 20 and 22, which play no direct role in the present invention, respectively comprise a proximal injection lumen, a distal lumen, and a thermistor lumen. These three lumens are utilized in a conventional manner to monitor various characteristics within the pulmonary artery and right heart into which the inflatable portion 24 of the catheter 10 is inserted as subsequently described.

Syringe 14 has a hollow, transparent plastic body 42 of an elongated cylindrical configuration. Body 42 has a forwardly disposed, conical inner or outlet endwall 44, and an open rear or outer end 46 having outwardly projecting finger support tabs 48 formed thereon. Extending axially outwardly from the forward endwall 44, and communicating with the interior of the syringe body 42, is a reduced diameter, hollow cylindrical outlet tube 50. Coaxially circumscribing the outlet tube 50 is a larger diameter hollow cylindrical connection collar 52 which projects outwardly from the endwall 44. The collar 52 is somewhat shorter than the outlet tube 50 and is internally threaded as at 54.

The catheter 12 is connectable to the syringe 14 by inserting the outlet tube 50 into the gas inlet passage 36 of the catheter inlet fitting 34 so that the connecting tabs 38 enter the syringe connecting collar 52. The syringe body 42 and the catheter inlet fitting 34 are then relatively rotated so that the connecting tabs 38 engage the internal threads 34 to thereby releasably lock the inlet fitting 34 to the connecting collar 52.

To pressurize gas within the syringe body 42 and force the gas into the balloon inflation lumen 16, the syringe 14 is provided with a plunger 56 which is coaxially received within the syringe body 42 for movement toward and away from the syringe body endwall 44 (as may be seen by comparing the solid line position of the plunger to its dotted line position 56$_a$) to respectively force gas from and draw gas into the syringe body. Plunger 56 has an elongated plastic body portion 58 defined in cross-section by four longitudinally extending transverse ribs 60 (see also FIG. 4). At its outer end the plunger body 58 is provided with a circular thumb flange 62, while at the inner end of the plunger body is a smaller diameter circular flange 64. Secured to the inner end of the plunger body 58, and abutting its inner end flange 64, is a rubber seal element 66 which slidably and sealingly engages the interior surface of the syringe body 42 and has a generally conically shaped inner end portion 68 that is complementarily configured relative to the endwall 44.

To utilize the syringe and catheter apparatus 10, the tube portion 24 thereof is inserted into and through a suitable vein, such as the jugular vein, until the distal end 28 of the insertion tube 24 is properly positioned within the superior vena cava. The syringe plunger 56 is then manually pushed toward the syringe body endwall 44 to inflate the balloon 30. Balloon 30 is then "floated" through the heart and into the pulmonary artery until a branch thereof is occluded by the inflated balloon. With a pulmonary artery branch blocked in this manner, a variety of conditions therein, such as the "wedge" pressure downstream from the distal tube end 28 may be measured and monitored. This initial measurement and monitoring (as well as subsequent measurement and monitoring) is effected by an oscilloscope which is operatively associated with the catheter and generates a trace pattern indicative of the arterial wedge pressure downstream from the inflated balloon.

After this initial wedge pressure reading has been taken, the balloon is deflated. However, the catheter is then normally left in its inserted position so that the balloon can be selectively reinflated to take subsequent wedge pressure and/or other readings. It is primarily in conjunction with these subsequent balloon inflations that the well-known problem of balloon over-pressurization, and concomitant bursting of a pulmonary artery branch can occur.

This problem can arise if, after the initial deflation of the balloon, the distal catheter end "migrates" into an arterial branch which is substantially smaller and/or weaker than the one the inflated balloon initially became wedged in and occluded. Subsequent inflation of the balloon in this smaller and/or weaker arterial branch, if not done with extreme care, can easily cause the arterial branch to rupture and cause very rapid death of the patient.

Arterial catheters, such as the representative catheter 12 depicted in FIG. 1, are typically designed (and so labeled) to receive up to a predetermined maximum volume of pressurized air (or other gas) from its associated syringe-such volume of gas being that which will fully inflate the balloon 30 or other inflatable element associated with the insertion tube 24. Subject to the expected variations in interior sizes of pulmonary arteries, and the strengths thereof, this overall volume design limitation is intended to safely limit the maximum balloon pressure.

As an example, the illustrated catheter 12 has a 1.5 cc volume design limitation. Typically, conventional syringes used in conjunction with catheters of this type have an internal body volume greater than the design volume of the catheter. This is due to the fact that it is convenient, and less expensive, for the apparatus manufacturer to utilize a single, standard-sized syringe body with a variety of catheters having varying volume design capacities. As an example, the syringe 14 depicted in FIG. 1 in conjunction with the 1.5 cc catheter 12 has a nominal gas discharge capacity of 5 cc-i.e., a gas discharge capacity substantially larger than the design limit of catheter 12.

In an attempt to safely "match" the over-sized syringe to the catheter, it has been conventional practice to provide the syringe with volume-limiting means which function to limit the maximum gas volume dischargeable therefrom to the nominal volume inlet capacity of the catheter. In conventional over-sized catheter syringes, such volume-limiting means are provided by forming in the side wall portion of the syringe body laterally inwardly directed, diametrically opposed projections 70 which are positioned forwardly of the open body end 46 and rearwardly of the plunger body flange 64. The projections 70 are normally formed by pressing heated cylindrical forming members against diametrically opposite sidewall portions of the syringe body to plastically deform such sidewall portions into the syringe body so that they project inwardly of the periphery 72 (FIG. 4) of the plunger body flange 64. Positioned in this manner, the inward projections 70 function as stop members which limit the rearward travel of the plunger within the syringe body.

In a conventionally constructed catheter syringe of this type, these projections are axially positioned on the syringe body so that the gas volume within the syringe body between the plunger seal element and the outlet endwall of the body is equal to the nominal volume capacity of the catheter. Thus, the dischargeable gas quantity of the syringe is precisely matched to the design volume capacity of the catheter. As illustrated in FIG. 1, this volume-limiting technique, via the previously described stop members 70, is incorporated into the improved syringe 14 of the present invention. However, for reasons subsequently described, the distance between the illustrated stop members 70 and the endwall 44 is greater than such distance in catheter syringes of conventional construction.

A modified conventional volume-limiting technique is also incorporated in the alternate embodiment 14$_a$ of the syringe 14 depicted in FIG. 1A, the syringe 14$_a$ being in all other regards identical to the syringe 14. In the syringe 14$_a$, the rearwardly disposed plunger stop members 70 are eliminated, and are replaced by a small vent opening 74 formed through the sidewall of the syringe body forwardly of the open rear end 46 thereof. It can be seen in FIG. 1A that with the plunger seal element 66 disposed rearwardly (i.e., leftwardly) of the opening 74, forward motion of the plunger 56 toward the opening 74 will not force pressurized gas from within the syringe body into the catheter lumen 16. Instead, such forward plunger motion will simply force gas from within the syringe body outwardly through the vent opening 74.

It is only when the forwardmost annular sealing surface 76 of the seal element 66 forwardly crosses the opening 74 that the plunger can force pressurized gas outwardly through the outlet end of the syringe and into the lumen 16. Accordingly, in conventional catheter syringes, the vent opening 74 is axially positioned along the length of the syringe body such that the volume between the opening and the outlet endwall of the syringe body is equal to the design volume capacity of the catheter. However, as in the case of the rear stop members 70 in syringe 14, the opening 74 in syringe 14$_a$ is spaced a greater distance rearwardly from the endwall 44 than it would be in a conventional syringe having the same gas discharge capacity.

In and of itself, however, neither of these conventional volume-limiting means (or other similar volume-limiting means) completely eliminates the potential problem of over pressurizing the balloon 30 when it is disposed within an artery having a lesser strength or internal dimension than anticipated when, for example, the uninflated catheter has distally migrated. In these instances, even though no more than the catheter design gas volume can be forced thereinto from the syringe, overpressurization of the catheter balloon, and arterial rupture, can occur.

Typically, upon each re-inflation of the catheter balloon the syringe operator must carefully and slowly depress the syringe plunger until the oscilloscope trace pattern indicates a "wedge" condition has been achieved—i.e., the inflating balloon has occluded the arterial branch in which it is lodged. At this point (which normally occurs with the balloon in a partially inflated condition) the syringe operator must desist from further inflating the balloon.

However, as is well known, the configurations of both "normal" and "wedge" trace patterns on the monitoring oscilloscope vary widely from patient to patient and can occasionally mislead even experienced syringe operators as to the existence of balloon occlusion in the artery branch in which the balloon is disposed. More specifically, the trace pattern may closely resemble one which is normally indicative of a nonoccluded artery when, in fact, full occlusion exists and further balloon inflation could rupture the artery. As but one example, an incompetent mitral valve can generate back pressure pulses which can misleadingly indicate that the distal catheter end is still "free" within the artery even though it is fully blocking the artery.

It is in these instances when great care must be exercised in inflating the catheter balloon. The syringe operator must be acutely aware of the resistance of the syringe plunger to further forward travel and stop its further travel if too great a resistance is encountered. In other words, the operator must rely on the "feel" of the syringe plunger to safeguard against arterial rupture because even in volume-limited syringes of conventional construction excessive pressures can easily be generated within the occluding balloon.

In a preferred embodiment thereof the present invention uniquely and substantially reduces these potential balloon overpressurization problems by providing within the body 42 of syringe 14 (or syringe 14$_a$ as the case may be) a stop member 80 which, in conjunction with the volume-limiting means 70 (or 76) affords the syringe the advantageous capability of being able to force into the catheter 12 up to its designed-for maximum volume of pressurized gas (to thereby fully inflate the balloon 30 during its blood-drawn initial "float" through the heart) while at the same time automatically reducing to a predetermined magnitude the pressure within the balloon 30 when it receives this maximum volume of gas from the syringe.

Referring to FIGS. 1-3, the stop member 80 has a hollow cylindrical body 82 whose external diameter is somewhat smaller than the internal diameter of the syringe body 42. At one end thereof the body 82 is circumferentially enlarged to define an annular end flange 84. The stop member 80 is coaxially disposed within a forward end portion of the syringe body so that the flange 84 abuts a radially outer portion of the conical endwall 44 and the opposite annular end surface 86 of the stop member faces the plunger seal element 66.

Interposed in this manner between the seal element 66 and the syringe outlet tube 50, the stop member 80 creates within the syringe body 42 a pressure absorption zone which defines an essentially inextensible enlargement of the gas-receiving interior of the catheter 12. Such pressure absorption zone comprises the annulus 88 circumscribing the stop member body 82, the interior 90 of the body 82, and the generally conical space 92 disposed between the flange 84 and the syringe body endwall 44. The end surface 86 of the stop member 80 engages and stops the plunger seal element 66 during forward movement thereof in a position (indicated at 66$_a$ in FIG. 1) spaced rearwardly from the syringe body endwall 44.

This end surface 86 is suitably spaced from the stop members 70 so that when the plunger seal element 66 moves from its solid line position to its dotted line position 66$_a$ a maximum of 1.5 cc of pressurized gas (i.e., the maximum design volume of the catheter 12) is forced through the stop member interior 90 and the outlet tube 50 into the lumen 16 and the insertion tube 24 to thereby fully inflate the balloon 30.

However, since the total effective volume of the gas receiving interior of the catheter 12 is increased by the pressure absorption zone volume created by the stop member 80, the resulting internal pressure within the balloon 30 is reduced by a preselected magnitude determined by the size of the stop member 80. By properly selecting the maximum attainable pressure within the balloon 30, the risk of rupturing an artery which is smaller or weaker than anticipated is substantially reduced. Importantly, such risk is effectively reduced without regard to how the plunger 56 is pushed or who is pushing it.

The syringe 14$_a$ of FIG. 1A is functionally identical to the syringe 14, in that it is both volume and pressure-limited, except that the volume-limiting wall opening 74 does not form a rearward mechanical stop for the plunger 56. Instead, as previously described, it functions (together with the forward stop member 80) to limit the "effective" stroke of the plunger since internal pressurization of the syringe body does not begin until the sealing surface 76 of the seal element forwardly traverses the wall opening 74.

It should be noted that the actual maximum stroke of the plunger 56 in syringe 14 (or the maximum "effective" plunger stroke in syringe 14$_a$) necessary to discharge the maximum design gas volume into the catheter 12 is at least somewhat longer than would otherwise be necessary in the absence of the stop member 80. This is due to the fact that the gas-receiving interior of the catheter 12 has been effectively increased by the volume of the pressure absorption zone defined by the stop member 80. Accordingly, more gas must be displaced within the syringe body by the plunger seal element 66 to flow the design volume of gas into the catheter, and the distance between the stop members 70 (or the opening 74) and the endwall 44 is concomitantly increased. It will be appreciated that the necessary spacing between the stop member end surface 86 and the rear stop members 70, or the side-wall opening 74, is determined by the total volume of the pressure absorption zone created by the stop member 80.

It will be readily appreciated that the stop member 80 may be given a variety of alternate configurations other than that depicted in FIG. 2. As but one example of such alternate configuration, an alternate forward stop member 80$_a$ (FIGS. 2A and 3A) may be provided which has a hollow cylindrical configuration of an external diameter just slightly smaller than the internal diameter of the syringe body 42 so that the stop member 80$_a$ is closely received in the syringe body adjacent its endwall 44 as cross-sectionally depicted in FIG. 3A. It can be seen that this embodiment of the forward stop member, when positioned within the syringe body, defines a radially inward enlargement of a forward axial portion thereof. Accordingly, instead of inserting the stop member 80$_a$ into the syringe body, a forward longitudinal portion of the body could simply be enlarged during its manufacture.

Alternatively, in conjunction with the modified syringe embodiment 14$_b$ illustrated in FIG. 5, inserts such as stop members 80 and 80$_a$ could be replaced by diametrically opposed, inwardly projecting forward stop portions 94 formed in the sidewall of the syringe body 42, in a manner similar to that used to form the stop portions 70 in FIG. 1, and positioned rearwardly of the syringe body endwall 44 and forwardly of the plunger seal element 66. In this instance, the pressure absorption zone would be defined by the interior syringe body volume 96 positioned between the outlet tube 50 and the forward conical face 68 of the plunger seal element 66 when it sealingly engages the forward stop members 94 as depicted in FIG. 5.

In the previously described embodiments of the improved syringe of the present invention, the unique pressure absorption zone was created within the syringe body by forward stop means therein such as the elements 80, 80$_a$ or 94. However, if desired, such pressure absorption zone may be formed externally to the syringe body. Referring now to FIG. 6, an alternate embodiment 10$_a$ of the syringe and catheter apparatus 10 is illustrated in which a modified syringe 14$_c$ is provided that is similar in construction to the previously, described syringes, and has volume-limiting means such as stops 70 or wall opening 74, but has removed therefrom the forward stop means. Accordingly, the conical end surface 68 of the plunger seal element 66 may be forced into engagement with the complementarily configured interior surface 44$_a$ of the outlet endwall 44.

The external pressure absorption zone is defined by a length of plastic tubing 96 which has an internal volume equal to the desired volume of the pressure absorption zone and is interconnectable between the syringe outlet tube 50 and the catheter inlet fitting 34. Specifically, the tubing 96 has a female inlet fitting 98 adapted to receive the outlet tube 50, and a male discharge fitting 100 adapted for insertion into the gas inlet passage 36 of the catheter inlet fitting 34. While the plastic tubing 96 is flexible, when it is operatively interconnected between the syringe and the catheter as previously described it defines an essentially inextensible enlargement of the gas-receiving interior of the catheter. In this manner, when the end face 68 of the plunger seal element 66 engages the interior surface 44$_a$ of the endwall 44 the 1.5 cc design gas volume will have been forced into the catheter, but the resulting balloon pressure will be lessened to a predetermined degree by the pressure absorption zone defined within the interconnecting tube 96. The syringe 14$_c$, like the previously described syringes 14, 14$_a$ and 14$_b$, is thus both volume and pressure-limited.

As previously mentioned, the present invention may be conveniently utilized in conjunction with a gas syringe having a "standard" body size with a total internal volume in excess of that needed to provide the catheter with its maximum design volume of gas to fully inflate its balloon element. By providing the standard syringe body with appropriate volume-limiting means (such as stops 70 or wall opening 74) together with the unique pressure reducing means of the present invention (such as the elements 80, 80$_a$, 94 or 96) it may be inexpensively converted to a volume and pressure-limited syringe such as the syringes 14, 14$_a$, 14$_b$ and 14$_c$. By appropriate correlation between the volume of the pressure absorption zone and the rearward spacing of the volume-limiting means, a standard size syringe body may be conveniently converted for use with catheters having a variety of maximum gas volume requirements.

However, if desired, the syringe body may be custom size for each catheter application so that the necessity for the previously described volume limiting means is eliminated. This could be achieved for example, by simply shortening the syringe body length so that (with the pressure reducing means in place) the resulting maximum effective available plunger stroke could discharge from the syringe only the design gas volume of the catheter.

It can be seen that the present invention provides an improved syringe and catheter apparatus having significantly enhanced operational safety characteristics. The maximum balloon pressure achievable with the volume and pressure-limited syringe may be reduced to a predetermined, safer level without the previous necessity of utilizing pressure relief valves, external inflatable elements or other conventional pressure limiting devices which are subject to wear and/or failure during use. Additionally, other than the normal necessity of monitoring the oscilloscope for the "wedge" trace pattern during reinflation of the catheter balloon, there is no need to otherwise monitor the pressure increase within the catheter, as with a mechanical pressure gauge, since the maximum pressure attainable therein is preset, and nonvariable, by virtue of the unique pressure absorption zone within the apparatus.

While the principles of the present invention are particularly well adapted for use in conjunction with the illustrated pulmonary artery catheter, it will be appreciated that such principles may also be utilized in other gas-operated catheter apparatus such as, for example, endotracheal catheters which are provided at their distal ends with inflatable cuff members.

The foregoing detailed description is to be clearly understood as being given by way of illustration and example only, the spirit and scope of the present invention being limited solely by the appended claims.

What is claimed is:

1. Improved syringe and catheter apparatus comprising:
   catheter means for internally blocking a body passage, said catheter means being adapted to internally receive a predetermined maximum volume of pressurized gas from a source thereof and having an inflatable portion insertable into the body passage for inflation therein by the pressurized gas received within said catheter means;
   syringe means operable to discharge up to said predetermined maximum volume of pressurized gas into the interior of said catheter means; and
   pressure reducing means positioned within said syringe means for defining an essentially inextensible enlargement of the gas-receiving interior of said catheter means, said enlargement functioning as a pressure absorption zone which reduces to a predetermined magnitude the maximum internal pressure within the gas receiving interior of said catheter means caused by receipt therein of said predetermined maximum volume of pressurized gas from said syringe means so that said predetermined maximum volume of pressurized gas may be forced into and retained within the gas-receiving interior of said catheter means without creating therein a pressure exceeding said predetermined magnitude thereof,
   said syringe means including a hollow syringe body and said pressure absorption zone being disposed within said body and bounded by an interior surface portion thereof,
   said syringe means further including a plunger disposed in said hollow syringe body and operative to force gas therein outwardly through an outlet thereof,
   said pressure reducing means including stop means, positioned within said hollow syringe body between said plunger and said outlet, for engaging and stopping said plunger in a spaced relationship with said outlet during movement of said plunger toward said outlet,
   said stop means defining an internal enlargement of said hollow syringe body.

2. The apparatus of claim 1 wherein:
   said internal enlargement is positioned adjacent said outlet.

3. The apparatus of claim 1 wherein:
   said internal enlargement is spaced apart from said outlet.

4. Improved syringe and catheter apparatus comprising:
   catheter means for internally blocking a body passage, said catheter means being adapted to internally receive a predetermined maximum volume of pressurized gas from a source thereof and having an inflatable portion insertable into the body passage for inflation therein by the pressurized gas received within said catheter means;
   syringe means operable to discharge up to said predetermined maximum volume of pressurized gas into the interior of said catheter means; and
   pressure reducing means positioned within said syringe means for defining an essentially inextensible enlargement of the gas-receiving interior of said catheter means, said enlargement functioning as a pressure absorption zone which reduces to a predetermined magnitude the maximum internal pressure within the gas receiving interior of said catheter means caused by receipt therein of said predetermined maximum volume of pressurized gas from said syringe means so that said predetermined maximum volume of pressurized gas may be forced into and retained within the gas-receiving interior of said catheter means without creating therein a pressure exceeding said predetermined magnitude thereof,
   said syringe means including a hollow syringe body and said pressure absorption zone being disposed within said body and bounded by an interior surface portion thereof,
   said syringe means further including a plunger disposed in said hollow syringe body and operative to force gas therein outwardly through an outlet thereof,
   said pressure reducing means including stop means, positioned within said hollow syringe body between said plunger and said outlet, for engaging and stopping said plunger in a spaced relationship with said outlet during movement of said plunger toward said outlet, said stop means comprising a hollow stop member disposed within said hollow syringe body.

5. Improved syringe and catheter apparatus comprising:
   catheter means for internally blocking a body passage, said catheter means being adapted to internally receive a predetermined maximum volume of pressurized gas from a source thereof and having an inflatable portion insertable into the body passage for inflation therein by the pressurized gas received within said catheter means;
   syringe means operable to discharge up to said predetermined maximum volume of pressurized gas into the interior of said catheter means; and
   pressure reducing means positioned within said syringe means for defining an essentially inextensible enlargement of the gas-receiving interior of said catheter means, said enlargement functioning as a pressure absorption zone which reduces to a predetermined magnitude the maximum internal pressure within the gas receiving interior of said catheter means caused by receipt therein of said predetermined maximum volume of pressurized gas from said syringe means so that said predetermined maximum volume of pressurized gas may be forced into and retained within the gas-receiving interior of said catheter means without creating therein a pressure exceeding said predetermined magnitude thereof, said syringe means including a hollow syringe body having an internal volume greater than said predetermined maximum volume of pressurized gas, a gas outlet formed in said hollow syringe body, and a plunger received in said hollow syringe body and operative to force gas therein outwardly through said gas outlet, said apparatus further comprising volume limiting means carried by said syringe body for limiting the volume of gas dischargeable by said plunger through said gas outlet to said predetermined maximum volume of pressurized gas, said hollow syringe body having a sidewall portion, and said volume limiting means comprising an opening formed through said sidewall portion and spaced apart from said gas outlet.

6. A syringe for use in internally pressurizing a catheter, comprising:

a hollow body adapted to receive a quantity of gas and having an outlet end operatively connectable to the catheter for discharging gas thereinto from within said body;

a plunger received in said body for movement toward and away from said outlet end thereof to respectively discharge gas through said outlet end and draw gas into said body; and pressure reducing means for limiting the pressure increase within the catheter to a predetermined magnitude when a predetermined maximum volume of gas is forced into the catheter from said syringe, said pressure reducing means including stop means, interposed between said plunger and said outlet end of said body, for engaging and stopping said plunger in a spaced relationship with said outlet end during movement of said plunger toward said outlet end, said stop means comprising a hollow stop member disposed within said body of said syringe.

7. The syringe of claim 6 wherein:
said stop member is adjacent said outlet end of said body of said syringe.

8. The syringe of claim 6 wherein:
said stop member has a generally cylindrical configuration and is coaxially disposed within said body of said syringe.

9. The syringe of claim 8 wherein:
said stop member is cross-sectionally smaller than the interior of said body and has a laterally projecting portion formed thereon.

10. The syringe of claim 9 wherein:
said laterally projecting portion is an annular flange.

11. The syringe of claim 10 wherein:
said annular flange is an end flange and is positioned adjacent said outlet end of said body of said syringe.

12. A syringe for use in internally pressurizing a catheter, comprising:

a hollow body adapted to receive a quantity of gas and having an outlet end operatively connectable to the catheter for discharging gas thereinto from within said body;

a plunger received in said body for movement toward and away from said outlet end thereof to respectively discharge gas through said outlet end and draw gas into said body; and pressure reducing means for limiting the pressure increase within the catheter to a predetermined magnitude when a predetermined maximum volume of gas is forced into the catheter from said syringe, said pressure reducing means including stop means, interposed between said plunger and said outlet end of said body, for engaging and stopping said plunger in a spaced relationship with said outlet end during movement of said plunger toward said outlet end, said stop means defining an internal enlargement of said body of said syringe.

13. The syringe of claim 12 wherein:
said internal enlargement is positioned adjacent said outlet end of said body of said syringe.

14. The syringe of claim 12 wherein:
said internal enlargement is spaced apart from said outlet end of said body of said syringe.

15. A syringe for use in internally pressurizing a catheter, comprising:

a hollow body adapted to receive a quantity of gas and having an outlet end operatively connectable to the catheter for discharging gas thereinto from within said body;

a plunger received in said body for movement toward and away from said outlet end thereof to respectively discharge gas through said outlet end and draw gas into said body; and pressure reducing means for limiting the pressure increase within the catheter to a predetermined magnitude when a predetermined maximum volume of gas is forced into the catheter from said syringe, said pressure reducing means including stop means, interposed between said plunger and said outlet end of said body, for engaging and stopping said plunger in a spaced relationship with said outlet end during movement of said plunger toward said outlet end, said stop means defining an internal enlargement of said body of said syringe, said internal enlargement being spaced apart from said outlet end of said body of said syringe, said internal enlargement comprising a generally facing duality of inwardly projecting wall portions of said body of said syringe.

16. A syringe for use in internally pressurizing a catheter, comprising:

a hollow body adapted to receive a quantity of gas and having an outlet end operatively connectable to the catheter for discharging gas thereinto from within said body;

a plunger received in said body for movement toward and away from said outlet end thereof to respectively discharge gas through said outlet end and draw gas into said body; and pressure reducing means for limiting the pressure increase within the catheter to a predetermined magnitude when a predetermined maximum volume of gas is forced into the catheter from said syringe, said pressure reducing means including stop means, interposed between said plunger and said outlet end of said body, for engaging and stopping said plunger in a spaced relationship with said outlet end during movement of said plunger toward said outlet end, the internal volume of said hollow body being greater than said predetermined maximum volume of gas and said syringe further comprising volume limiting means, carried by said body of said syringe, for cooperating with said plunger to limit the volume of gas dischargeable through said outlet end of said body of said syringe to said predetermined maximum volume of gas, said volume limiting means including an opening extending laterally through a wall portion of said body spaced apart from said outlet end thereof.

17. A syringe for use in internally pressurizing a catheter, comprising:

a hollow body adapted to receive a quantity of gas and having an outlet end operatively connectable to the catheter for discharging gas thereinto from within said body;

a plunger received in said body for movement toward and away from said outlet end thereof to respectively discharge gas through said outlet end and draw gas into said body; and pressure reducing means for limiting the pressure increase within the catheter to a predetermined magnitude when a predetermined maximum volume of gas is forced into the catheter from said syringe, said pressure reducing means including stop means, interposed between said plunger and said outlet end of said body, for engaging and stopping said plunger in a spaced relationship with said outlet end during movement of said plunger toward said outlet end, the internal volume of said hollow body being greater than said predetermined maximum volume of gas and said syringe further comprising volume limiting means, carried by said body of said syringe, for cooperating with said plunger to limit the volume of gas dischargeable through said outlet end of said body of said syringe to said predetermined maximum volume of gas, said volume limiting means including stop means for limiting movement of said plunger away from said outlet end of said body of said syringe, said stop means being defined by an internal enlargement of said body of said syringe.

18. A syringe for use in internally pressurizing a catheter, comprising:

a hollow body adapted to receive a quantity of gas and having an outlet end operatively connectable to the catheter for discharging gas thereinto from within said body;

a plunger received in said body for movement toward and away from said outlet end thereof to respectively discharge gas through said outlet end and draw gas into said body; and pressure reducing means for limiting the pressure increase within the catheter to a predetermined magnitude when a predetermined maximum volume of gas is forced into the catheter from said syringe, said pressure reducing means including stop means, interposed between said plunger and said outlet end of said body, for engaging and stopping said plunger in a spaced relationship with said outlet end during movement of said plunger toward said outlet end, the internal volume of said hollow body being greater than said predetermined maximum volume of gas and said syringe further comprising volume limiting means, carried by said body of said syringe, for cooperating with said plunger to limit the volume of gas dischargeable through said outlet end of said body of said syringe to said predetermined maximum volume of gas, said volume limiting means including stop means for limiting movement of said plunger away from said outlet end of said body of said syringe, said stop means being defined by an internal enlargement of said body of said syringe, said internal enlargement comprising a generally facing duality of inwardly projecting wall portions of said body of said syringe.

* * * * *